United States Patent [19]
Paschal

[11] Patent Number: 6,116,741
[45] Date of Patent: *Sep. 12, 2000

[54] SURGICAL MICROSCOPE OPERATING DRAPE AND METHODS OF OPERATION AND MANUFACTURE THEREOF

[75] Inventor: Patti B. Paschal, Columbus, Miss.

[73] Assignee: DEKA Medical, Incorporated, Columbus, Miss.

[ * ] Notice: This patent issued on a continued prosecution application filed under 37 CFR 1.53(d), and is subject to the twenty year patent term provisions of 35 U.S.C. 154(a)(2).

[21] Appl. No.: 09/042,062

[22] Filed: Mar. 13, 1998

[51] Int. Cl.$^7$ ............................. G03B 11/04; B65D 85/38
[52] U.S. Cl. ......................... 359/510; 359/511; 359/513; 359/900; 206/316.1; 600/121; 600/124
[58] Field of Search ..................................... 359/510, 511, 359/513, 514, 900; 206/305, 316.1, 316.2, 316.3; 600/121, 124, 125

[56] References Cited

U.S. PATENT DOCUMENTS

| | | | |
|---|---|---|---|
| 3,528,720 | 9/1970 | Treace | 359/510 |
| 3,698,791 | 10/1972 | Walchle et al. | 359/510 |
| 3,796,477 | 3/1974 | Geraci | 359/511 |
| 4,176,701 | 12/1979 | Welgan | 359/511 |
| 4,385,812 | 5/1983 | Wille et al. | 359/511 |
| 4,799,779 | 1/1989 | Mesmer | 359/510 |
| 5,155,624 | 10/1992 | Flagler | 359/511 |
| 5,311,358 | 5/1994 | Pederson et al. | 359/510 |
| 5,467,223 | 11/1995 | Cleveland, Jr. et al. | 359/510 |
| 5,853,363 | 12/1998 | Vought | 359/510 |

OTHER PUBLICATIONS

"Microscope Drapes" Technical Information sheets on "Microdrape®" 6 pages.
"Innovation By Design . . . Microscope Drapes" Technical Information sheets from Microtek Medical: 5 pages; 1994.
"Innovation By Design . . . Universal Microscope Drape" Technical Information Sheets from Microtek Medical for Product No. 6920; 2 pages.
"Opmi® Drape" Technical Information sheets from Carl Zeiss, Inc. 7 pages; 1992.

*Primary Examiner*—Ricky D. Shafer
*Attorney, Agent, or Firm*—Thompson & Knight, L.L.P.

[57] ABSTRACT

For use with a surgical microscope having an objective lens barrel protruding therefrom, drapes, methods of draping the microscope and methods of manufacturing the drapes. In one embodiment, a drape includes: (1) a sheet, having a sheet aperture therethrough, that covers at least a portion of the surgical microscope, (2) a rigid, planar seal mount, coupled to the sheet and having a mount aperture therethrough that aligns with the sheet aperture and (3) an elastomeric sheet seal, coupled to the planar seal mount and having a dilatable seal aperture therethrough that has a constricted diameter less than the mount aperture, aligns with the mount aperture, expands to receive the objective lens barrel therethrough and elastically constricts about the objective lens barrel.

21 Claims, 5 Drawing Sheets

SURGICAL MICROSCOPE OPERATING DRAPE AND METHODS OF OPERATION AND MANUFACTURE THEREOF

TECHNICAL FIELD OF THE INVENTION

The present invention is directed, in general, to surgical drapes and, more specifically, to a surgical microscope operating drape and methods of draping a surgical microscope and manufacturing the drape.

BACKGROUND OF THE INVENTION

A surgical field, as found in a typical hospital's operating room, is an environmentally controlled area where the risk of infection from naturally occurring organisms is minimized. The environment's "cleanliness" is controlled by limiting the introduction of infection-creating organisms and other contaminants by maintaining strict controls over the personnel and equipment that are present in the surgical field.

One way to minimize the risk of infection to surgical patients in the operating room is with the use of equipment and personnel drapes. The drapes are placed over the patient, operating room staff and/or equipment to form a sterile barrier, keeping any microorganisms and contaminants that could cause infections from migrating to exposed tissue and open wounds. Also, the drapes prevent the bodily fluids, such as blood or lymphatic fluids, which are encountered during most surgical procedures from settling on the operating room's furniture and equipment. These fluids may become airborne when, for instance, a vein or artery is severed. In some instances, these fluids themselves may contain contaminants, such as hepatitis or staphylococcus, which can be transmitted to the other persons in the room. Likewise, these fluids may also settle on furniture or equipment of the room, which then become contaminated and a hazard to those persons who must work in the room. Instead, the airborne fluids will ultimately settle on the drapes and not on the draped furniture and equipment.

The advancement of medical procedures has correspondingly created a demand for more advanced medical equipment. Specifically, the surgical microscope has become an integral part of the operating room. As surgical procedures are becoming increasingly more complex and addressing ever smaller parts of the human anatomy, the surgical microscope has allowed the surgeon unprecedented observation of the region being operated upon. This has allowed more complex procedures to be attempted with an increased probability of success.

The surgical microscope is typically a ceiling-mounted device that may be raised or lowered and positioned over any part of the patient's body. The surgical microscope often has multiple eyepieces that permit the surgeon and others to simultaneously view the magnified area under the microscope's objective lens.

A microscope drape, used to create a sterile barrier, is typically affixed to the microscope at the lens housing of the objective lens, to orient the drape with respect to the remaining structure of the microscope. Once the microscope drape is attached to the objective lens barrel, other portions of the drape may be spread and positioned to cover the remainder of the microscope structure.

The objective lens barrels for comparable surgical microscopes of different manufacturers are often of different sizes. Thus, a microscope drape that fits the objective lens barrel of one microscope may not fit the objective lens barrel of a similar microscope made by a different manufacturer. Consequently, a larger and more expensive inventory of several different drapes is necessary to accommodate the different microscope objective lens barrels. Furthermore, several surgical microscopes have objective lens barrels that are close in size. Therefore, if an incorrect drape is accidentally used and the fit is not secure, sudden slippage of the mounting device, such as a mounting ring, into the surgical field could occur during an operation, possibly resulting in serious complications to the patient.

Therefore, what is needed in the art is a more easily installed, flexible, lower cost alternative to such prior art surgical microscope operating drapes. Further, what is needed in the art are improved methods of draping a surgical microscope and methods of manufacturing a surgical microscope operating drape.

SUMMARY OF THE INVENTION

The construction and use of one kind of surgical microscope operating drape is described in co-pending application Ser. No. 08/901,510, filed Jul. 28, 1997, entitled "Surgical Microscope Operating Drape and Methods of Operation and Manufacture Thereof" commonly assigned with the present application and incorporated herein by reference. The present invention seeks further to improve upon the constricting band in the draping sheet that is shown in that co-pending application. An improved, constricted opening would be one which could be even more quickly and positively installed on, or removed from, an operating microscope.

To address the above-discussed deficiencies of the prior art and to improve upon the invention described in the co-pending application, it is a primary object of the present invention to provide a more universal microscope drape.

In the attainment of the above-described primary object, the present invention provides, for use with a surgical microscope having an objective lens barrel protruding therefrom, drapes, methods of draping the microscope and methods of manufacturing the drapes. In one embodiment, a drape includes: (1) a sheet, having a sheet aperture therethrough, that covers at least a portion of the surgical microscope, (2) a rigid, planar seal mount, coupled to the sheet and having a mount aperture therethrough that aligns with the sheet aperture and (3) an elastomeric sheet seal, coupled to the planar seal mount and having a dilatable seal aperture therethrough that has a constricted radius less than the mount aperture, aligns with the mount aperture, expands to receive the objective lens barrel therethrough and elastically constricts about the objective lens barrel.

The present invention therefore introduces a surgical microscope operating drape having features that allow the sheet to be more flexible in the types of microscopes that it can accommodate. For purposes of the present invention, "sheet" is defined broadly to include not only sheets in planar form, but also in cylindrical or tubular form (irrespective of whether the ends of the cylinder or tube are open or closed). "Sheet" is further defined to include extrudable materials (such as plastic) as well as woven materials (such as cloth). The rigid, planar seal mount may extend sufficiently to provide handles (perhaps with handle apertures) for fitting the drape to, and removing the drape from, the microscope.

In one embodiment of the present invention, the drape further comprises a transparent objective lens cover, separate from the sheet and having a flexible barrel adapter, the flexible barrel adapter expandable to fit about and cover the objective lens barrel, the sheet and the objective lens cover cooperating to cover the portion of the surgical microscope, including the objective lens barrel. Because they are wholly separate, relatively few sheets and objective lens covers may be combined to fit a wide range of microscopes, thereby avoiding the significant expense of the prior art drapes discussed above.

Alternatively, the present invention can employ an objective lens cover (perhaps without a flexible barrel adapter) that is coupled to the planar seal mount, yielding a unitary microscope drape. The elastomeric sheet seal advantageously provides sufficient frictional contact with the barrel of the microscope's objective lens to hold the objective lens cover in place.

In one embodiment of the present invention, the objective lens aperture has an elastic band thereabout to render the objective lens cover elastically deformable. In an embodiment to be illustrated and described, the elastic band is bonded (perhaps by gluing or sewing) to the sheet and extends entirely about the objective lens aperture. This need not be the case, however.

In one embodiment of the present invention, the dilatable seal lens aperture forms a particle-resistant seal about the objective lens barrel. A particle-resistant seal, while advantageously protecting the microscope against contamination, is not necessary to the present invention.

In one embodiment of the present invention, the objective lens cover is composed in part of plastic. Alternatively, the objective lens cover may be composed of another transparent material, such as glass or quartz.

In one embodiment of the present invention, the flexible barrel adapter comprises a resilient gasket. The resilient gasket expands to the extent necessary to allow the objective lens barrel to be inserted into the objective lens cover. Those skilled in the art will perceive other means by which the barrel adapter may be made flexible without requiring a flexible gasket.

In one embodiment of the present invention, the flexible barrel adapter fits over the sheet proximate the objective lens aperture. Alternatively, the flexible barrel adapter may simply abut the sheet or allow a portion of the objective lens barrel to be exposed.

In one embodiment of the present invention, the drape further comprises at least one hook-and-pile fastener (commonly known as VELCRO®, manufactured by the Dupont Corporation), coupled to the sheet, that fixes the sheet to a portion of the surgical microscope. Those skilled in the art are familiar with many acceptable ways to fix a drape to a microscope apart from a hook-and-pile fastener.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
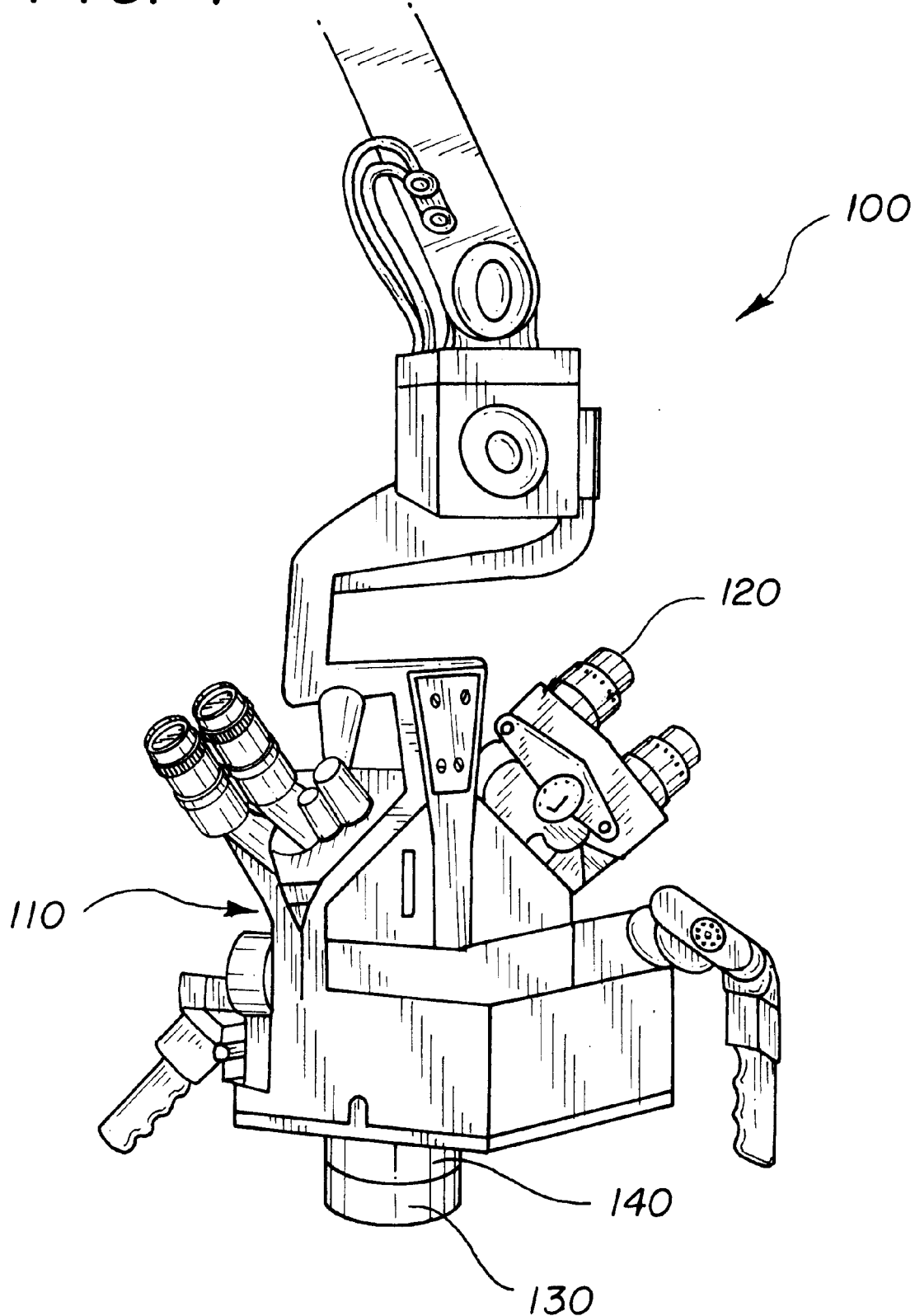
FIG. 1 illustrates an exemplary surgical operating microscope.

Referring initially to FIG. 1, illustrated is an exemplary surgical operating microscope. The surgical operating microscope, generally designated 100, has a main body 110 with a plurality of eyepieces (one of which is designated 120) extending upwardly from the main body 110. Also shown is an objective lens 130 coupled to an objective lens barrel 140. The objective lens barrel 140 projects downwardly from the main body 110 such that, when the microscope 100 is placed over the patient's body, the objective lens 130 points down toward the body. The eyepieces 120 provide the surgeon and/or other surgical team members precise visual control of the region of the patient undergoing an operation through the objective lens 130.

Figure 2:
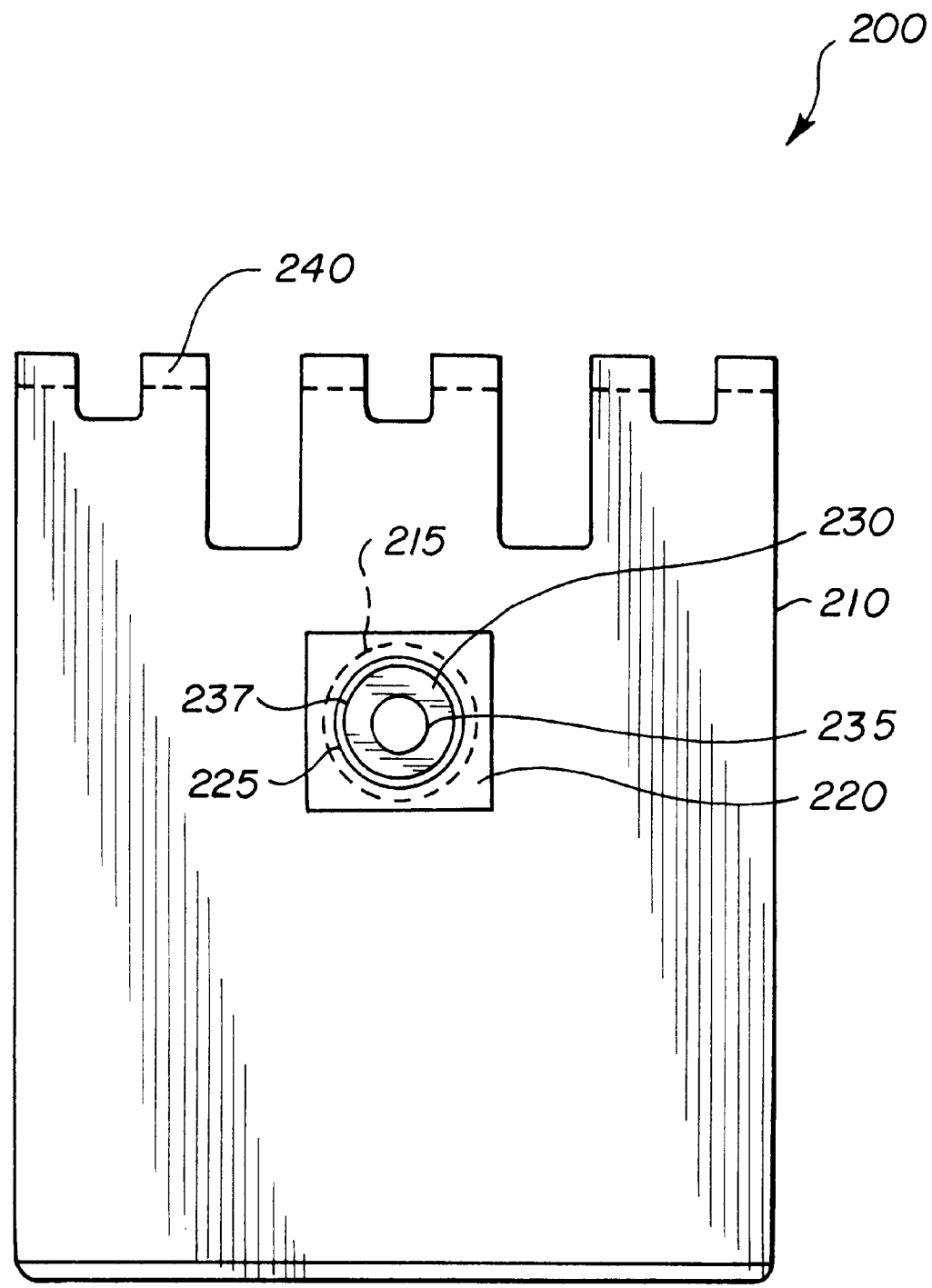
FIG. 2 illustrates a plan view of one embodiment of a microscope drape constructed according to the principles of the present invention.

Turning now to FIG. 2, illustrated is a plan view of one embodiment of a microscope drape constructed according to the principles of the present invention. The microscope drape, generally designated 200, comprises a sheet 210, a planar seal mount 220, an elastomeric sheet seal 230, and a plurality of fasteners (one of which is designated 240).

In a preferred embodiment, the sheet 210 is formed as a tube having a single closed end, that has a sheet aperture 215 opening through the sheet 210. A plurality of fasteners 240 are shown attached to both ends of the sheet 210. The sheet 210 (again, preferably in the form of a tube) has dimensions that allow the sheet 210 substantially to cover the surgical operating microscope main body 110. Those skilled in the art are aware that surgical operating microscopes 100 vary in size and dimensions and that the dimensions of the sheet 210 are selected to accommodate the largest microscope 100 dimensions in use. The materials that may be used for the sheet 210, as those skilled in the art are aware, are typically those materials that are suitable for use in an operating room environment, e.g., a heat-resistant polymer.

The planar seal mount 220 is attached (coupled in some manner) to the sheet 210 and located proximate the sheet aperture 215. The planar seal mount 220 comprises a mount aperture 225 which is aligned with the sheet aperture 215. In the illustrated embodiment, the planar seal mount 220 is roughly square in shape, however, one skilled in the art will recognize that circular, rectangular or other shapes may be desirable and are within the scope of the present invention. In fact, if it is desired to include handles on the planar seal mount 220, the planar seal mount 220 may advantageously be elongated.

Affixed to the planar seal mount 220 is an elastomeric sheet seal 230 with a dilatable seal aperture 235 therethrough. The dilatable seal aperture 235 is constructed with a constricted diameter 237 less than the diameter of the smallest objective lens barrel 140 of commercial operating microscopes 100. The dilatable seal aperture 235 allows the sheet aperture 215 to accommodate objective lens barrels 140 of varying diameters from the smallest diameter objective lens barrel 140 to the largest diameter objective lens barrel 140 that is commonly in use. When fully constricted (relaxed) the diameter 237 is slightly smaller than the smallest diameter objective lens barrel 140. When fully stretched about the largest diameter objective lens barrel 140 that is commonly in use the seal 230 closes securely about the lens barrel 140.

In one embodiment, the elastomeric sheet seal 230 forms a particle-resistant seal when stretched over the objective lens barrel 140. The particle-resistant seal prevents particles or droplets from passing between the elastomeric sheet seal 230 and the objective lens barrel 140 and contaminating the main body 110 of the microscope 100.

The sheet 210 is dressed onto the microscope 100 by lifting the rigid seal mount 220 around the objective lens barrel 140. The elastomeric sheet seal 230 deforms about the objective lens barrel 140 to form a seal. The sheet 210 is then wrapped about the microscope body 110 leaving the eyepieces 120 exposed and the sheet 210 is secured with fasteners 240. The fasteners 240 in the illustrated embodiment are hook-and-pile fasteners (widely known as VELCRO®, one brand name under which such fasteners are commercially available), however, other fastening methods and devices are well known in the art, such as ties or safety pins.

In one advantageous embodiment, the sheet 210 may be stored within a toroidal bag (not shown) attached to the planar seal mount 220. Once the objective lens barrel 140 is inserted through the dilatable seal aperture 235, the toroidal bag can be opened, freeing the sheet 210 and allowing the sheet 210 to be unfurled about and cover the surgical operating microscope main body 110.

Figure 3B:
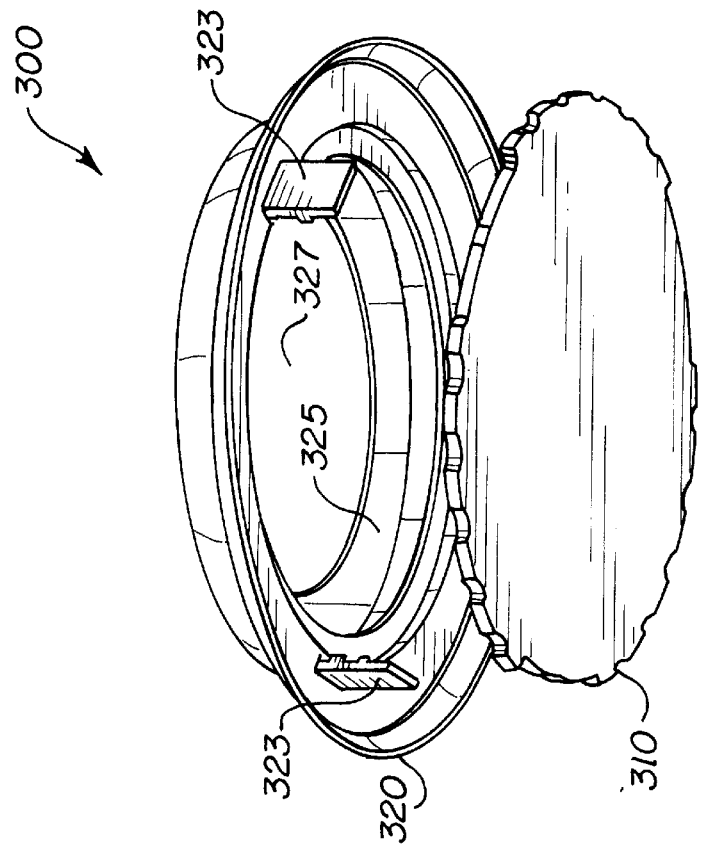
FIGS. 3A and 3B illustrate upper and lower exploded isometric views of one embodiment of a microscope objective lens cover for use with the microscope drape of FIG. 2.
Figure 3A:
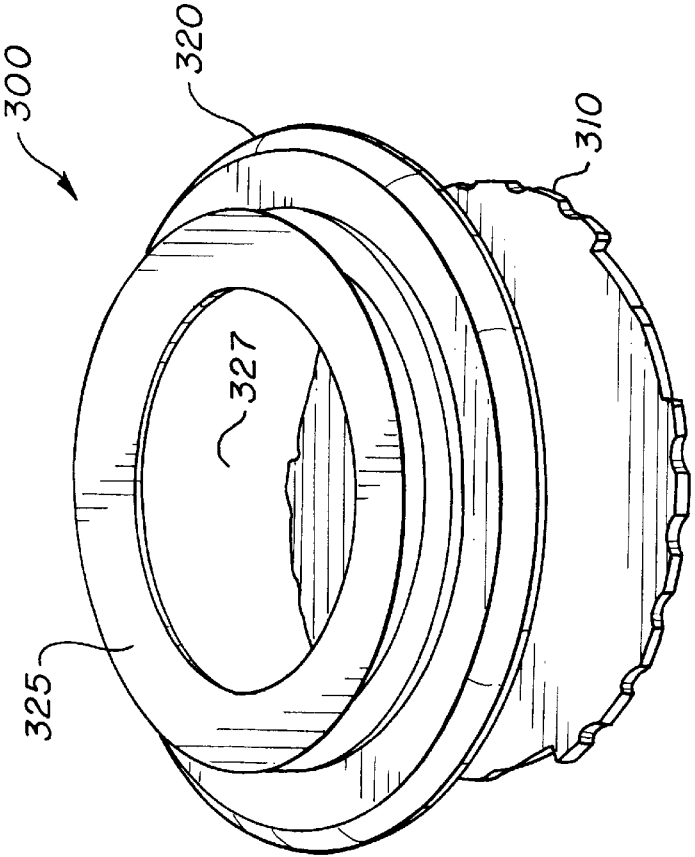

Turning now to FIGS. 3A and 3B, illustrated are upper and lower exploded isometric views of one embodiment of a microscope objective lens cover for use with the microscope drape of FIG. 2. The microscope objective lens cover 300 comprises a transparent objective lens cover 310, and a flexible barrel adaptor 320 that combine to provide a protective cover for the objective lens 130 from fluids and contaminants usually encountered during a surgical procedure. The flexible barrel adaptor 320 includes a resilient gasket 325 formed radially about a barrel adaptor aperture 327. The lens cover 310 may be composed of plastic or any other transparent material, such as glass or quartz. The barrel adaptor 320 may be composed of plastic or any other suitable material, and need not be transparent. Alternatively, the lens cover 310 and barrel adaptor 320 may be composed of a combination of materials, such as glass and plastic, respectively. The resilient gasket 325 is sized so that the gasket 325 expands and firmly contacts the lens barrel 140 when the flexible barrel adaptor 320 is pressed onto the lens barrel 140, thus holding the barrel adaptor 320 in place. Those skilled in the art are aware of several materials with elastic properties, such as rubber, which may be used for the resilient gasket 325. The barrel adaptor 320 further comprises a plurality of lens supports 323 which hold the transparent objective lens cover 310 in place.

In an alternative embodiment, the flexible barrel adapter 320 may simply abut the sheet 210 or allow a portion of the objective lens barrel 140 to be exposed. In yet another alternative embodiment, the flexible barrel adaptor 320 may be permanently affixed to the planar seal mount 220, so that the entire assembly may be installed in a single motion over the objective lens barrel 140.

Figure 4B:
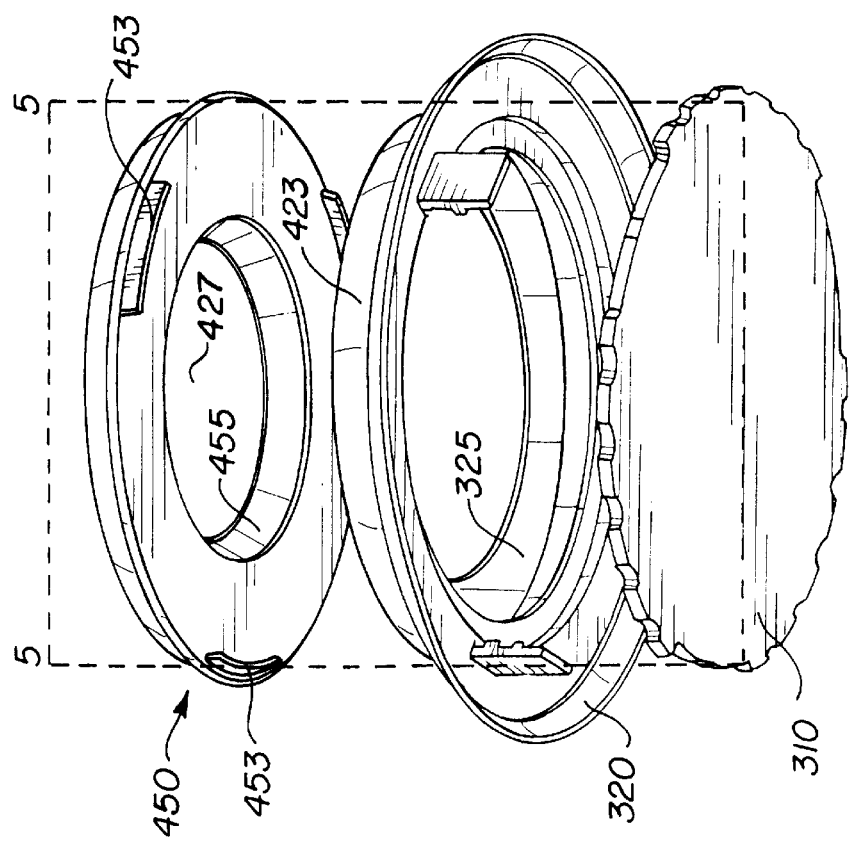
FIGS. 4A and 4B illustrate exploded isometric views of one embodiment of a small lens adaptor for use with the objective lens cover of FIGS. 3A and 3B.
Figure 4A:
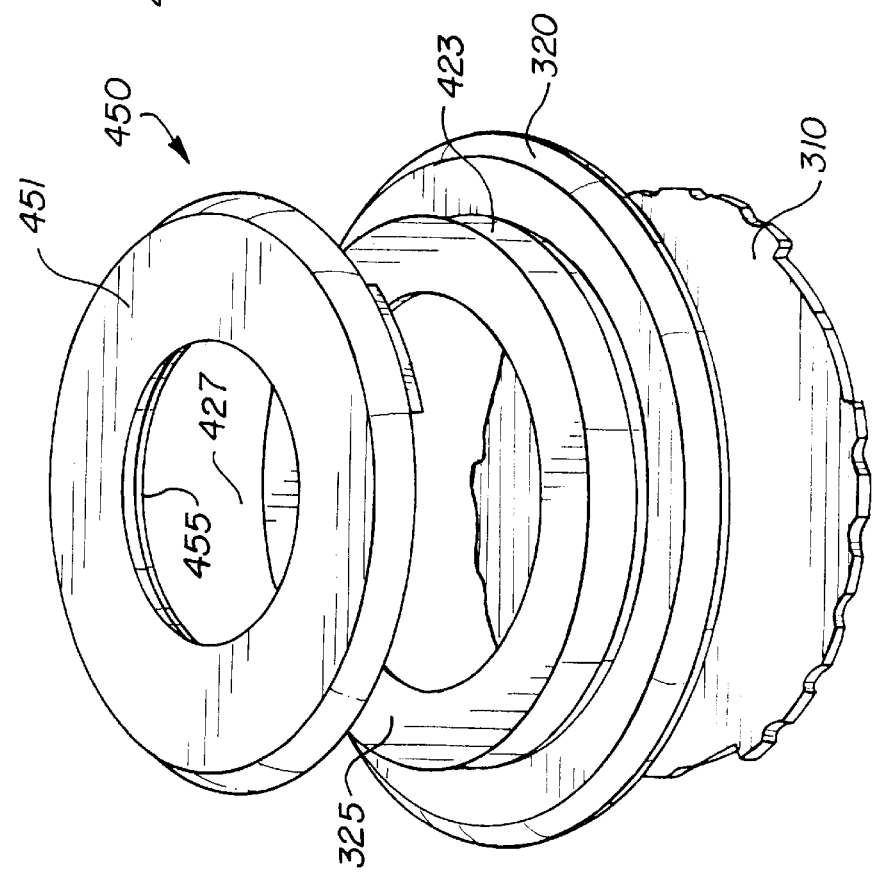

Referring now to FIG. 4A and 4B, illustrated are exploded isometric views of one embodiment of a small lens adaptor for use with the objective lens cover of FIGS. 3A and 3B. The small lens adaptor 450 comprises an adaptor body 451 and a small lens resilient gasket 455 formed radially about a small lens barrel adaptor aperture 427. The adaptor body 451 and gasket 455 are formed of the same materials as the flexible barrel adaptor 320 and resilient gasket 325 of FIGS. 3A and 3B.

The small lens resilient gasket 455 functions for smaller diameter lenses in an manner analogous to the resilient gasket 325 of FIGS. 3A and 3B.

The adaptor body 451 is constructed so that a plurality of adaptor clips 453 engage securely with a friction fit about the outer surface 423 of the flexible barrel adaptor 320. This embodiment enables the barrel adaptor 320 to fit smaller diameter lenses than it could otherwise accommodate. In the preferred embodiment, the lens diameter ranges for the barrel adaptor 320 and the small lens barrel adaptor 350 overlap slightly, e.g., a barrel adaptor 320 range from 2" to 3" with a small lens barrel adaptor 350 range from 1.5" to 2.125". One skilled in the art readily understands that the sizes specified are not limiting to the scope of the present invention, but are provided solely for illustrative purposes.

Figure 5A:
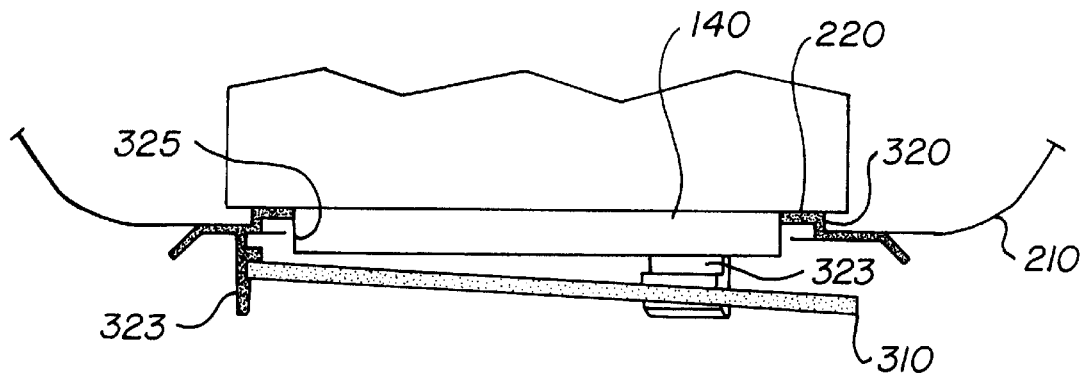
FIGS. 5A, 5B and 5C illustrate sectional views of one embodiment of the microscope drape and objective lens cover of FIG. 4 along the plane 5—5 installed on three objective lenses of different size.
Figure 5B:
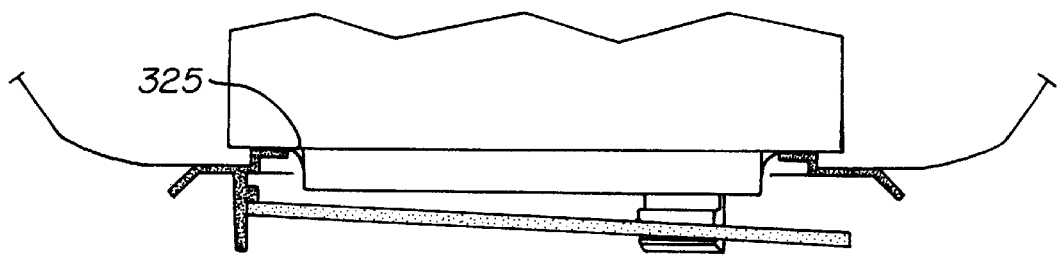
Figure 5C:
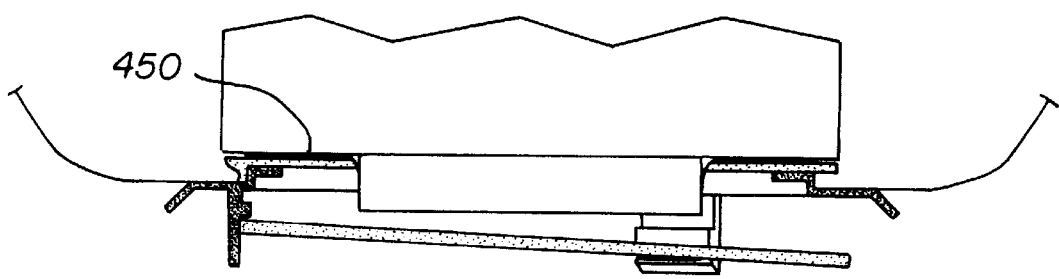

Referring now to FIGS. 5A, 5B and 5C, illustrated are sectional views of one embodiment of the microscope drape and objective lens cover of FIG. 4 along the plane 5—5 installed on three different size objective lenses. When in place, the resilient gasket 325 of the flexible barrel adaptor 320 flexibly engages the objective lens barrel 140. In the illustrated embodiment, the planar seal mount 220 and flexible barrel adaptor 320 are both mechanically bonded to the sheet 210 so that the assembly may be installed in a single motion.

FIG. 5A illustrates installation of the microscope drape over a lens at the maximum capacity of the flexible barrel adaptor 320. FIG. 5B illustrates installation of the microscope drape over a lens at the minimum capacity of the flexible barrel adaptor 320. One skilled in the art will note the difference by observing the shape of the resilient gasket 325 in the two illustrations. FIG. 5C illustrates installation of the microscope drape over a lens employing the small lens adaptor 450 of FIGS. 4A and 4B.

From the above, it is apparent that the present invention provides, for use with a surgical microscope having an objective lens barrel protruding therefrom, drapes, methods of draping the microscope and methods of manufacturing the drapes. In one embodiment, a drape includes: (1) a sheet, having a sheet aperture therethrough, that covers at least a portion of the surgical microscope, (2) a rigid, planar seal mount, coupled to the sheet and having a mount aperture therethrough that aligns with the sheet aperture and (3) an elastomeric sheet seal, coupled to the planar seal mount and having a dilatable seal aperture therethrough that has a constricted radius less than the mount aperture, aligns with the mount aperture, expands to receive the objective lens barrel therethrough and elastically constricts about the objective lens barrel.

Although the present invention and its advantages have been described in detail, those skilled in the art should understand that they can make various changes, substitutions and alterations herein without departing from the spirit and scope of the invention in its broadest form.

What is claimed is:

1. For use with a surgical microscope having an objective lens barrel protruding therefrom, a drape, comprising:

a sheet, having a sheet aperture therethrough, that covers at least a portion of said surgical microscope;

a rigid, essentially flat seal mount, coupled to said sheet and having a mount aperture therethrough that aligns with said sheet aperture; and an essentially flat elastomeric sheet seal, coupled to said seal mount and having a dilatable seal aperture therethrough that has a constricted diameter less than said mount aperture, aligns with said mount aperture, expands to receive said objective lens barrel therethrough and elastically constricts about said objective lens barrel.

2. The drape as recited in claim 1 further comprising a transparent objective lens cover, separate from said sheet and having a flexible barrel adapter, said flexible barrel adapter expandable to fit about and cover said objective lens barrel, said sheet and said objective lens cover cooperating to cover said portion of said surgical microscope, including said objective lens barrel.

3. The drape as recited in claim 2 wherein said objective lens cover is composed in part of plastic.

4. The drape as recited in claim 2 wherein said flexible barrel adapter comprises a resilient gasket.

5. The drape as recited in claim 2 wherein said flexible barrel adapter fits over said sheet proximate said seal aperture.

6. The drape as recited in claim 1 wherein said elastomeric sheet seal forms a particle-resistant seal about said objective lens barrel.

7. The drape as recited in claim 1 further comprising at least one hook-and-pile fastener, coupled to said sheet, that fixes said sheet to said portion of said surgical microscope.

8. A method of draping a surgical microscope having an objective lens barrel protruding therefrom, comprising the steps of:

covering at least a portion of said surgical microscope with a sheet having a sheet aperture therethrough, said sheet further coupled to a rigid, essentially flat seal mount, said seal mount having a mount aperture therethrough that aligns with said sheet aperture;

inserting said objective lens barrel through a dilatable seal aperture in an essentially flat elastomeric sheet seal coupled to said seal mount, said dilatable seal aperture having a constricted diameter less than said mount aperture, aligning with said mount aperture, expanding to receive said objective lens barrel therethrough and elastically constricting about said objective lens barrel.

9. The method as recited in claim 8 further comprising the step of covering said objective lens barrel with a transparent objective lens cover separate from said sheet and having a flexible barrel adapter, said flexible barrel adapter expandable to fit about said objective lens barrel, said sheet and said objective lens cover cooperating to cover said portion of said surgical microscope, including said objective lens barrel.

10. The method as recited in claim 9 wherein said objective lens cover is composed in part of plastic.

11. The method as recited in claim 9 wherein said flexible barrel adapter comprises a resilient gasket.

12. The method as recited in claim 9 wherein said step of covering said objective lens barrel comprises the step of fitting said flexible barrel adapter over said sheet proximate said dilatable seal aperture.

13. The method as recited in claim 8 further comprising the step of forming a particle-resistant seal about said objective lens barrel.

14. The method as recited in claim 8 further comprising the step of fixing said sheet to said portion of said surgical microscope with at least one hook-and-pile fastener coupled to said sheet.

15. A method of manufacturing a drape for a surgical microscope having an objective lens barrel protruding therefrom, comprising the steps of:

creating a sheet aperture in a sheet, said sheet adapted to cover at least a portion of said surgical microscope;

coupling a rigid, essentially flat seal mount to said sheet, said seal mount having a mount aperture therethrough that aligns with said sheet aperture;

coupling an essentially flat elastomeric sheet seal to said seal mount, said sheet seal having a dilatable seal aperture therethrough that has a constricted diameter less than said mount aperture, aligns with said mount aperture, expands to receive said objective lens barrel therethrough and elastically constricts about said objective lens barrel.

16. The method as recited in claim 15 further comprising the step of forming a transparent objective lens cover, separate from said sheet and having a flexible barrel adapter, said flexible barrel adapter expandable to fit about and cover said objective lens barrel, said sheet and said objective lens cover cooperating to cover said portion of said surgical microscope, including said objective lens barrel.

17. The method as recited in claim 16 wherein said step of forming comprises the step of composing said objective lens cover in part of plastic.

18. The method as recited in claim 16 wherein said step of forming comprises the step of depositing a resilient gasket proximate said flexible barrel adapter.

19. The method as recited in claim 16 wherein said flexible barrel adapter is sized to fit over said sheet proximate said dilatable seal aperture.

20. The method as recited in claim 15 wherein said dilatable seal aperture is sized to form a particle-resistant seal about said objective lens barrel.

21. The method as recited in claim 15 further comprising the step of coupling at least one hook-and-pile fastener to said sheet, said at least one hook-and-pile fastener allowing said sheet to be fixed to said portion of said surgical microscope.

* * * * *